United States Patent [19]

Norris et al.

[11] Patent Number: 5,618,696

[45] Date of Patent: Apr. 8, 1997

[54] HUMAN KUNITZ-TYPE PROTEASE INHIBITOR AND VARIANTS THEREOF

[75] Inventors: Fanny Norris; Kjeld Norris, both of Hellerup; Søren E. Bjørn, Lyngby; Lars C. Petersen, Hørsholm; Ole H. Olsen, Brønshøj, all of Denmark; Donald C. Foster; Cindy A. Sprecher, both of Seattle, Wash.

[73] Assignee: Novo Nordisk A/S, Bagsvaerd, Denmark

[21] Appl. No.: 384,489

[22] Filed: Feb. 6, 1995

Related U.S. Application Data

[63] Continuation of Ser. No. 21,534, filed as PCT/DK93/00006, Jan. 7, 1993, abandoned.

[30] Foreign Application Priority Data

Jan. 7, 1992 [WO] WIPO ............... PCT/DK92/00003

[51] Int. Cl.$^6$ ............... C12N 15/00; C12N 15/12; C12N 1/19; C07K 14/81
[52] U.S. Cl. ............... 435/69.2; 530/300; 530/324; 536/23.5; 435/254.2; 435/320.1; 514/12; 930/250
[58] Field of Search ............... 530/300, 324; 536/23.5; 514/12; 435/69.2, 240.2, 252.3, 254.2, 320.1; 930/250

[56] References Cited

U.S. PATENT DOCUMENTS

| 4,966,852 | 10/1990 | Wun et al. | 435/69.2 |
| 5,106,833 | 4/1992 | Broze, Jr. et al. | 514/12 |
| 5,122,594 | 6/1992 | Yoshida et al. | 435/69.2 |
| 5,126,322 | 6/1992 | Collins et al. | 514/9 |

FOREIGN PATENT DOCUMENTS

| 0339942 | 4/1989 | European Pat. Off. . |
| 3724570 | 7/1987 | Germany . |

OTHER PUBLICATIONS

Day et al, "Bacterial expression of . . . TFPI . . . " *Thromb. Res.* 68: 369–381 (Dec. 1992).

*Primary Examiner*—Stephen G. Walsh
*Assistant Examiner*—Robert C. Hayes
*Attorney, Agent, or Firm*—Steve T. Zelson, Esq.; Cheryl H. Agris, Esq.

[57] ABSTRACT

The present invention relates to a human Kunitz-type protease inhibitor comprising the following amino acid sequence > Asp Leu Leu Pro Asn Val Cys Ala Phe Pro Met Glu Lys Gly Pro
> Cys Gln Thr Tyr Met Thr Arg Trp Phe Phe Asn Phe Glu Thr
> Gly Glu Cys Glu Leu Phe Ala Tyr Gly Gly Cys Gly Gly Asn
> Ser Asn Asn Phe Leu Arg Lys Glu Lys Cys Glu Lys Phe Cys
> Lys Phe Thr(SEQ ID NO:1)

or a variant thereof with protease inhibitor properties.

17 Claims, 3 Drawing Sheets

HUMAN KUNITZ PROTEASE INHIBITOR DOMAINS

```
ITI-1:  KEDSCQLGYSAGPCMGMTSRYFYNGTSMACETFQYGGCMGNGNNFVTEKECLQTCRTV
ITI-2:  TVAACNLPIVRGPCRAFIQLWAFDAVKGKCVLFPYGGCQGNGNKFYSEKECREYCGVP
APPI :  VREVCSEQAETGPCRAMISRWYFDVTEGKCAPFFYGGCGGNRNNFDTEEYCMAVCGSA
TFPI1:  MHSFCAFKADDGPCKAIMKRFFFNIFTRQCEEFIYGGCEGNQNRFESLEECKKMCTRD
TFPI2:  KPDFCFLEEDPGICRGYITRYFYNNQTKQCERFKYGGCLGNMNNFETLEECKNICEDG
TFPI3:  GPSWCLTPADRGLCRANENRFYYNSVIGKCRPFKYSGCGGNENNFTSKQECLRACKKG
α3-VI:  ETDICKLPKDEGTCRDFILKWYYDPNTKSCARFWYGGCGGNENKFGSQKECEKVCAPV

APROT:  RPDFCLEPPYTGPCKARIIRYFYNAKAGLCQTFVYGGCRAKRNNFKSAEDCMRTCGGA
              I              * *     II
```

| | |
|---|---|
| ITI-1(2) | : Inter alpha trypsin inhibitor KPI-domain 1(2). |
| APPI | : Alzheimer's disease amyloid protein precursor KPI-domain. |
| TFPI1(2,3) | : Tissue factor pathway inhibitor KPI-domain 1(2,3). |
| α3-VI | : C-Terminal KPI-domain of alpha 3 chain of type VI collagen. |
| APROT | : Bovine Basic pancreatic trypsin inhibitor, BPTI or aprotinin. |

Fig. 1

Kunitz domæne PCR-primers

A:  5'  GTTGGAATTCGGNCCNTG(T/C)AA(A/G)G   3'   23-mer

B:  5'  GTTGGAATTCGGNCCNTG(T/C)CG         3'   21-mer

C:  5'  GTTGGAATTCGGNNT(T/C)TG(T/C)AA(A/G)G   3'   23-mer

E:  5'  GTTGGAATTCGGNNT(A/G)TG(T/C)AA(A/G)G   3'   23-mer

F:  5'  GTTGGAATTCGGNNT(T/C)TG(T/C)CG         3'   21-mer

H:  5'  GTTGGAATTCGGNNT(A/G)TG(T/C)CG         3'   21-mer

X:  5'  GGTTTCTAGA(A/G)CANCC(A/G)CC(A/G)TA   3'   22-mer

Y:  5'  GGTTTCTAGA(A/G)CANCC(T/C)CC(A/G)TA   3'   22-mer

Z:  5'  GGTTTCTAGA(A/G)CANCC(A/G)CT(A/G)TA   3'   22-mer

Fig. 2

HUMAN KUNITZ-TYPE PROTEASE INHIBITOR AND VARIANTS THEREOF

This application is a continuation application of application Ser. No. 08/021,534, filed as PCT/DK93/00006 Jan. 7, 1993 (now abandoned), the contents of which are incorporated herein by reference.

FIELD OF INVENTION

The present invention relates to a novel human Kunitz-type protease inhibitor and variants thereof, DNA encoding the novel inhibitor or variants, a method of producing the novel inhibitor or variants and a pharmaceutical composition containing the novel inhibitor or variants.

BACKGROUND OF THE INVENTION

Polymorphonuclear leukocytes (neutrophils or PMNs) and mononuclear phagocytes (monocytes) play an important part in tissue injury, infection, acute and chronic inflammation and wound healing. The cells migrate from the blood to the site of inflammation and, following appropriate stimulation, they release oxidant compounds ($O_2\bullet$, $O_2$—, $H_2O_2$ and HOCl) as well as granules containing a variety of proteolytic enzymes. The secretory granules contain, i.a., alkaline phosphatase, metalloproteinases such as gelatinase and collagenase and serine proteases such as neutrophil elastase, cathepsin G and proteinase 3.

Latent metalloproteinases are released together with tissue inhibitor of metalloproteinase (TIMP). The activation mechanism has not been fully elucidated, but it is likely that oxidation of thiol groups and/or proteolysis play a part in the process. Also, free metalloproteinase activity is dependent on inactivation of TIMP.

In the azurophil granules of the leukocytes, the serine proteases neutrophil elastase, cathepsin G and proteinase-3 are packed as active enzymes complexed with glucosaminoglycans. These complexes are inactive but dissociate on secretion to release the active enzymes. To neutralize the protease activity, large amounts of the inhibitors $\alpha_1$-proteinase inhibitor ($\alpha_1$-PI) and $\alpha_1$-chymotrypsin inhibitor ($\alpha_1$-ChI) are found in plasma. However, the PMNs are able to inactivate the inhibitors locally. Thus, $\alpha_1$-PI which is the most important inhibitor of neutrophil elastase is sensitive to oxidation at the reactive center (Met- 358) by oxygen metabolites produced by triggered PMNs. This reduces the affinity of $\alpha_1$-PI for neutrophil elastase by approximately 2000 times.

After local neutralization of $\alpha_1$-PI, the elastase is able to degrade a number of inhibitors of other proteolytic enzymes. Elastase cleaves $\alpha_1$-ChI and thereby promotes cathepsin G activity. It also cleaves TIMP, resulting in tissue degradation by metalloproteinases. Furthermore, elastase cleaves antithrombin III and heparin cofactor II, and tissue factor pathway inhibitor (TFPI) which probably promotes clot formation. On the other hand, the ability of neutrophil elastase to degrade coagulation factors is assumed to have the opposite effect so that the total effect of elastase is unclear. The effect of neutrophil elastase on fibrinolysis is less ambiguous. Fibrinolytic activity increases when the elastase cleaves the plasminogen activator inhibitor and the $\alpha_2$ plasmin inhibitor. Besides, both of these inhibitors are oxidated and inactivated by $O_2$ metabolites.

PMNs contain large quantities of serine proteases, and about 200 mg of each of the leukocyte proteases are released daily to deal with invasive agents in the body. Acute inflammation leads to a many-fold increase in the amount of enzyme released. Under normal conditions, proteolysis is kept at an acceptably low level by large amounts of the inhibitors $\alpha_1$-PI, $\alpha_1$-ChI and $\alpha_2$ macroglobulin. There is some indication, however, that a number of chronic diseases is caused by pathological proteolysis due to overstimulation of the PMNs, for instance caused by autoimmune response, chronic infection, tobacco smoke or other irritants, etc.

Aprotinin (bovine pancreatic trypsin inhibitor) is known to inhibit various serine proteases, including trypsin, chymotrypsin, plasmin and kallikrein, and is used therapeutically in the treatment of acute pancreatitis, various states of shock syndrome, hyperfibrinolytic hemorrhage and myocardial infarction (cf., for instance, J. E. Trapnell et al, *Brit. J. Surg.* 61, 1974, p. 177; J. McMichan et al., *Circulatory shock* 9, 1982, p. 107; L. M. Auer et al., *Acta Neurochir.* 49, 1979, p. 207; G. Sher, *Am. J. Obstet. Gynecol.* 129, 1977, p. 164; and B. Schneider, *Artzneim.-Forsch.* 26, 1976, p. 1606). Administration of aprotinin in high doses significantly reduces blood loss in connection with cardiac surgery, including cardiopulmonary bypass operations (cf., for instance, B. P. Bidstrup et al., *J. Thorac. Cardiovasc. Surg.* 97, 1989, pp. 364–372; W. van Oeveren et al., *Ann. Thorac. Surg.* 44, 1987, pp. 640–645). It has previously been demonstrated (cf. H. R. Wenzel and H. Tschesche, *Angew. Chem. Internat. Ed.* 20, 1981, p. 295) that certain aprotinin analogues, e.g. aprotinin(1–58, Val15) exhibits a relatively high selectivity for granulocyte elastase and an inhibitory effect on collagenase, aprotinin (1–58, Ala15) has a weak effect on elastase, while aprotinin (3–58, Arg15, Ala17, Ser42) exhibits an excellent plasmakallikrein inhibitory effect (cf. WO 89/10374).

However, when administered in vivo, aprotinin has been found to have a nephrotoxic effect in rats, rabbits and dogs after repeated injections of relatively high doses of aprotinin (Bayer, *Trasylol, Inhibitor of proteinase*; E. Glaser et al. in "Verhandlungen der Deutschen Gesellschaft für Innere Medizin, 78. Kongress", Bergmann, München, 1972, pp. 1612–1614). The nephrotoxicity (i.a. appearing in the form of lesions) observed for aprotinin might be ascribed to the accumulation of aprotinin in the proximal tubulus cells of the kidneys as a result of the high positive net charge of aprotinin which causes it to be bound to the negatively charged surfaces of the tubuli. This nephrotoxicity makes aprotinin less suitable for clinical purposes, in particular those requiring administration of large doses of the inhibitor (such as cardiopulmonary bypass operations). Besides, aprotinin is a bovine protein which may therefore contain one or more epitopes which may give rise to an undesirable immune response on administration of aprotinin to humans.

It is therefore an object of the present invention to identify human protease inhibitors of the same type as aprotinin (i.e. Kunitz-type inhibitors) with a similar inhibitor profile or modified to exhibit a desired inhibitor profile.

SUMMARY OF THE INVENTION

The present invention relates to a novel human Kunitz-type protease inhibitor comprising the following amino acid sequence > Asp Leu Leu Pro Asn Val Cys Ala Phe Pro Met Glu Lys Gly Pro
> Cys Gln Thr Tyr Met Thr Arg Trp Phe Phe Asn Phe Glu Thr
> Gly Glu Cys Glu Leu Phe Ala Tyr Gly Gly Cys Gly Gly Asn
> Ser Asn Asn Phe Leu Arg Lys Glu Lys Cys Glu Lys Phe Cys
> Lys Phe Thr (SEQ ID No. 1)

or a variant thereof with protease inhibitor properties.

In another aspect, the present invention relates to a variant of this inhibitor comprising the following amino acid sequence $X^1$ Asn Val Cys Ala Phe Pro Met Glu $X^2$ Gly $X^3$ Cys $X^4$ $X^5$ $X^6$ $X^7$ $X^8$ $X^9$ Trp Phe Phe Asn Phe Glu Thr Gly Glu Cys Glu Leu Phe $X^{10}$ Tyr Gly Gly Cys $X^{11}$ $X^{12}$ $X^{13}$ Ser Asn Asn Phe $X^{14}$ $X^{15}$ $X^{16}$ Glu Lys Cys Glu Lys Phe Cys Lys Phe $X^{17}$ (SEQ ID No. 2)

wherein $X^1$ represents H or 1–5 naturally occurring amino acid residues except Cys, $X^2$–$X^{16}$ each independently represents a naturally occurring amino acid residue except Cys, and $X^{17}$ represents OH or 1–5 naturally occurring amino acid residues except Cys, with the proviso that at least one of the amino acid residues $X^1$–$X^{17}$ is different from the corresponding amino acid residue of the native sequence.

In the present context, the term "naturally occurring amino acid residue" is intended to indicate any one of the 20 commonly occurring amino acids, i.e. Ala, Val, Leu, Ile Pro, Phe, Trp, Met, Gly, Ser, Thr, Cys, Tyr, Asn, Gln, Asp, Glu, Lys, Arg and His.

The novel inhibitor was isolated from a human genomic DNA library by homology PCR (polymerase chain reaction) cloning. The amino acid sequences of known human Kunitz-type protease inhibitor domains were aligned together with that of aprotinin, and two regions, I and II, corresponding to aprotinin amino acid residues 12–16 and 35–38, respectively, were identified. Degenerate PCR primers were designed corresponding to homology region I and degenerate PCR primers were designed corresponding to homology region II. The PCR primers carried a 5'-extension containing a restriction recognition site for cloning purposes.

From the PCR experiment involving two of the primers a DNA sequence corresponding to a novel Kunitz-type protease inhibitor domain was identified. This DNA sequence was used as a probe for the isolation of the full length DNA sequence by screening a human genomic cosmid library. The isolation procedure is described in further detail in example 1 below with reference to FIGS. 1 and 2. In the following, the novel inhibitor is referred to a HKI B9.

By substituting one or more amino acids in one or more of the positions indicated above, it may be possible to change the inhibitor profile of HKI B9 so that it preferentially inhibits neutrophil elastase, cathepsin G and/or proteinase-3. Furthermore, it may be possible to construct variants which specifically inhibit enzymes involved in coagulation or fibrinolysis (e.g. plasmin or plasma kallikrein) or the complement cascade.

One advantage of HKI B9 is that it has a net charge of zero as opposed to aprotinin which, as indicated above, has a strongly positive net charge. It is therefore possible to construct variants of the invention with a lower positive net charge than aprotinin, thereby reducing the risk of kidney damage on administration of large doses of the variants. Another advantage is that, contrary to aprotinin, it is a human protein (fragment) so that undesired immunological reactions on administration to humans are significantly reduced.

BRIEF DESCRIPTION OF THE DRAWINGS

FIG. 1 shows a comparison of human Kunitz protease inhibitor domains from a number of different proteins.

Figure 3:
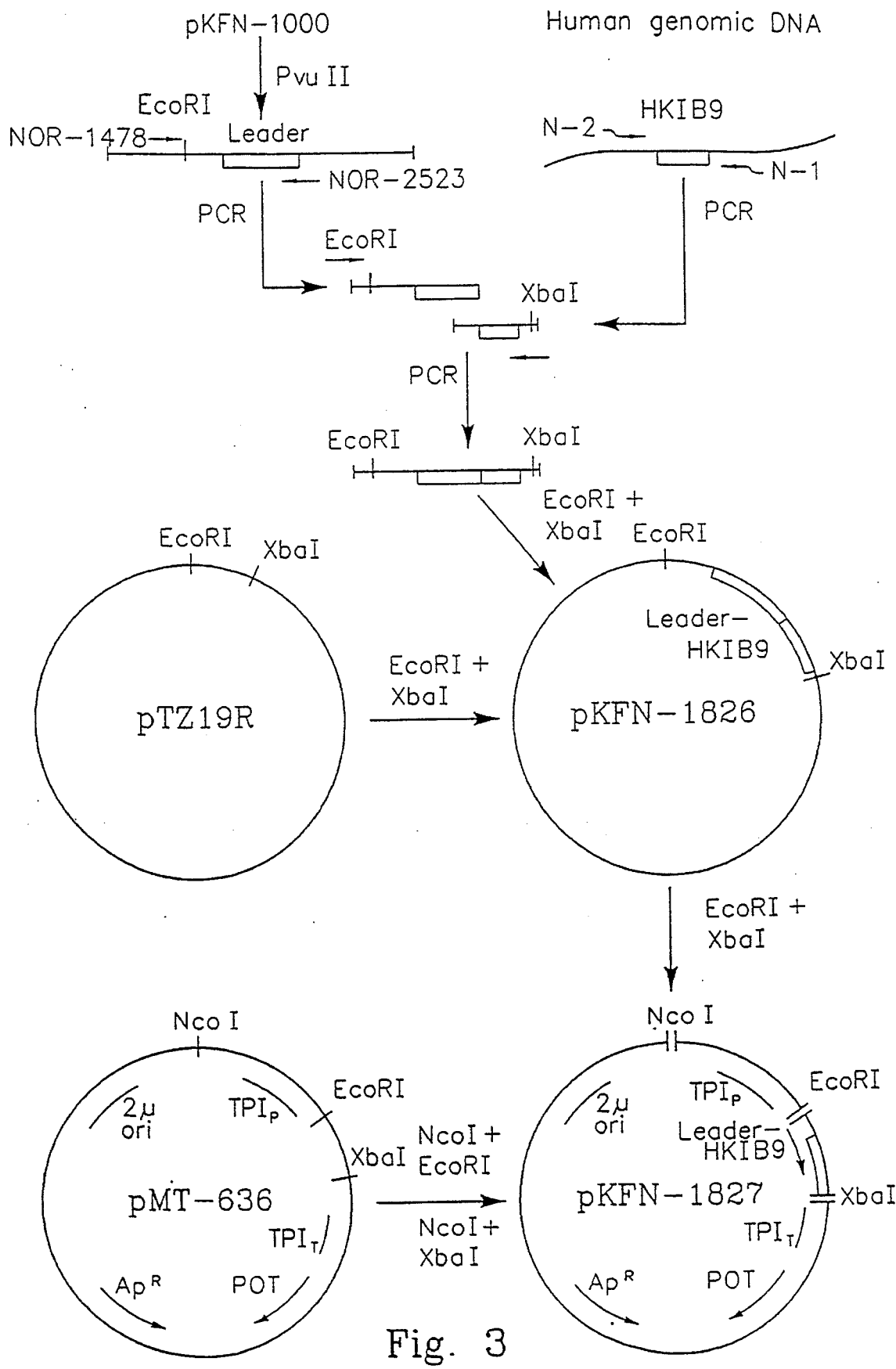

ITI-1 and 2: Inter alpha trypsin inhibitor KPI-domains 1 and 2 (SEQ. ID NOS: 10 AND 11);

APPI: Alzheimer's disease amyloid protein precursor KPI-domain (SEQ. ID NO: 12);

TFPI1, 2, and 3: Tissue factor pathway inhibitor KPI domains 1, 2 and 3 (SEQ. ID NOS: 13, 14 and 15);

α3-VI: C-terminal KPI-domain of alpha 3 chain of type VI collagen (SEQ. ID NO: 16)

APROT: Bovine basic pancreatic trypsin inhibitor, BPTI or aprotinin (SEQ. ID NO: 17)

FIG. 2 illustrates Kunitz domain DCR primers. A:SEQ. ID NO: 18; B:SEQ. ID NO.: 19; C:SEQ. ID NO: 20; C:SEQ ID NO: 20; E:SEQ ID NO: 21; F:SEQ ID NO: 22; H:SEQ ID NO: 23; X:SEQ ID NO: 24; Y:SEQ ID NO: 25; Z:SEQ ID NO.: 26.

FIG. 3 illustrates the construction of plasmid pKFN-1827.

DETAILED DISCLOSURE OF THE INVENTION

Examples of preferred variants of HKI B9 are variants wherein $X^1$ is Asp-Leu-Leu-Pro; or wherein $X^2$ is an amino acid residue selected from the group consisting of Ala, Arg, Thr, Asp, Pro, Glu, Lys, Gln, Ser, Ile and Val, in particular wherein $X^2$ is Thr or Lys; or wherein $X^3$ is an amino acid residue selected from the group consisting of Pro, Thr, Leu, Arg, Val and Ile, in particular wherein $X^3$ is Pro or Ile; or wherein $X^4$ is an amino acid residue selected from the group consisting of Lys, Arg, Val, Thr, Ile, Leu, Phe, Gly, Ser, Met, Trp, Tyr, Gln, Asn and Ala, in particular wherein $X^4$ is Lys, Val, Leu, Ile, Thr, Met, Gln or Arg; or wherein $X^5$ is an amino acid residue selected from the group consisting of Ala, Gly, Thr, Arg, Phe, Gln and Asp, in particular wherein $X^5$ is Ala, Thr, Asp or Gly; or wherein $X^6$ is an amino acid residue selected from the group consisting of Arg, Ala, Lys, Leu, Gly, His, Ser, Asp, Gln, Glu, Val, Thr, Tyr, Phe, Asn, Ile and Met, in particular wherein $X^6$ is Arg, Phe, Ala, Leu or Tyr; or wherein $X^7$ is an amino acid residue selected from the group consisting of Ile, Met, Gln, Glu, Thr, Leu, Val and Phe, in particular wherein $X^7$ is Ile; or wherein $X^8$ is an amino acid residue selected from the group consisting of Ile, Thr, Leu, Asn, Lys, Ser, Gln, Glu, Arg, Pro and Phe, in particular wherein $X^8$ is Ile or Thr; or wherein $X^9$ is an amino acid residue selected from the group consisting of Arg, Ser, Ala, Gln, Lys and Leu, in particular wherein $X^9$ is Arg; or wherein $X^{10}$ is an amino acid residue selected from the group consisting of Gln, Pro, Phe, Ile Lys, Trp, Ala, Thr, Leu, Ser, Tyr, His, Asp, Met, Arg and Val, in particular wherein $X^{10}$ is Val or Ala; or wherein $X^{11}$ is an amino acid residue selected from the group consisting of Gly, Met, Gln, Glu, Leu, Arg, Lys, Pro and Asn, in particular wherein $X^{11}$ is Arg or Gly; or wherein $X^{12}$ is Ala or Gly; or wherein $X^{13}$ is an amino acid residue selected from the group consisting of Lys, Asn and Asp, in particular wherein $X^{13}$ is Lys or Asn; or wherein $X^{14}$ is an amino acid residue selected from the group consisting of Val, Tyr, Asp, Glu, Thr, Gly, Leu, Ser, Ile, Gln, His, Asn, Pro, Phe, Met, Ala, Arg, Trp and Lys, in particular wherein $X^{14}$ is Lys or Leu; or wherein $X^{15}$ is Arg, Ser or Thr; or wherein $X^{16}$ is an amino acid residue selected from the group consisting of Glu, Lys, Gln and Ala, in particular wherein $X^{16}$ is Lys or Ala; or wherein $X^{17}$ is Thr. In a preferred embodiment, $X^1$ is Asp-Leu-Leu-Pro and $X^{17}$ is Thr, while $X^2$–$X^{16}$ are as defined above.

Variants of HKI B9 of the invention should preferably not contain a Met residue in the protease binding region (i.e. the amino acid residues represented by $X^3$–$X^{14}$). By analogy to $α_1$-PI described above, a Met residue in any one of these positions would make the inhibitor sensitive to oxidative inactivation by oxygen metabolites produced by PMNs, and conversely, lack of a Met residue in these positions should render the inhibitor more stable in the presence of such oxygen metabolites.

A currently preferred variant of the invention is one in which the amino acid residues located at the protease-binding site of the Kunitz inhibitor (i.e. $X^4$–$X^{14}$ corresponding to positions 13, 15, 16, 17, 18, 19, 20, 34, 39, 40, 41 and 46 of aprotinin) are substituted to the amino acids present in the same positions of native aprotinin. This variant comprises the following amino acid sequence Asp Leu Leu Pro Asn Val Cys Ala Phe Pro Met Glu Lys Gly Pro
Cys Lys Ala Arg Ile Ile Arg Trp Phe Phe Asn Phe Glu Thr Gly
Glu Cys Glu Leu Phe Val Tyr Gly Gly Cys Arg Ala Lys Ser
Asn Asn Phe Lys Ser Lys Glu Lys Cys Glu Lys Phe Cys Lys
Phe Thr (SEQ ID No. 3)

In another aspect, the invention relates to a DNA construct encoding a human Kunitz-type inhibitor or variant thereof according to the invention. The DNA construct of the invention may be prepared synthetically by established standard methods, e.g. the phosphoamidite method described by S. L. Beaucage and M. H. Caruthers, *Tetrahedron Letters* 22, 1981, pp. 1859–1869, or the method described by Matthes et al., *EMBO Journal* 3, 1984, pp. 801–805. According to the phosphoamidite method, oligonucleotides are synthesized, e.g. in an automatic DNA synthesizer, purified, annealed, ligated and cloned in suitable vectors.

Alternatively, it is possible to use genomic or cDNA coding for HKI B9 (e.g. obtained by screening a genomic library as described above). The DNA sequence may be modified at one or more sites corresponding to the site(s) at which it is desired to introduce amino acid substitutions, e.g. by site-directed mutagenesis using synthetic oligonucleotides encoding the desired amino acid sequence for homologous recombination in accordance with well-known procedures.

In a still further aspect, the invention relates to a recombinant expression vector which comprises a DNA construct of the invention. The recombinant expression vector may be any vector which may conveniently be subjected to recombinant DNA procedures, and the choice of vector will often depend on the host cell into which it is to be introduced. Thus, the vector may be an autonomously replicating vector, i.e. a vector which exists as an extrachromosomal entity, the replication of which is independent of chromosomal replication, e.g. a plasmid. Alternatively, the vector may be one which, when introduced into a host cell, is integrated into the host cell genome and replicated together with the chromosome(s) into which it has been integrated.

In the vector, the DNA sequence encoding HKI B9 or a variant thereof of the invention should be operably connected to a suitable promoter sequence. The promoter may be any DNA sequence which shows transcriptional activity in the host cell of choice and may be derived from genes encoding proteins either homologous or heterologous to the host cell. Examples of suitable promoters for directing the transcription of the DNA encoding the inhibitor of the invention in mammalian cells are the SV 40 promoter (Subramani et al., *Mol. Cell Biol.* 1, 1981, pp. 854–864), the MT-1 (metallothionein gene) promoter (Palmiter et al., *Science* 222, 1983, pp. 809–814) or the adenovirus 2 major late promoter. Suitable promoters for use in yeast host cells include promoters from yeast glycolytic genes (Hitzeman et al., *J. Biol. Chem.* 255, 1980, pp. 12073–12080; Alber and Kawasaki, *J. Mol. Appl. Gen.* 1, 1982, pp. 419–434) or alcohol dehydrogenase genes (Young et al., in *Genetic Engineering of Microorganisms for Chemicals* (Hollaender et al, eds.), Plenum Press, New York, 1982), or the TPI1 (U.S. Pat. No. 4,599,311) or ADH2-4c (Russell et al., *Nature* 304, 1983, pp. 652–654) promoters. Suitable promoters for use in filamentous fungus host cells are, for instance, the ADH3 promoter (McKnight et al., *The EMBO J.* 4, 1985, pp. 2093–2099) or the tpiA promoter.

The DNA sequence encoding the inhibitor of the invention may also be operably connected to a suitable terminator, such as the human growth hormone terminator (Palmiter et al., op. cit.) or (for fungal hosts) the TPI1 (Alber and Kawasaki, op. cit.) or ADH3 (McKnight et al., op. cit.) promoters. The vector may further comprise elements such as polyadenylation signals (e.g. from SV 40 or the adenovirus 5 Elb region), transcriptional enhancer sequences (e.g. the SV 40 enhancer) and translational enhancer sequences (e.g. the ones encoding adenovirus VA RNAs).

The recombinant expression vector of the invention may further comprise a DNA sequence enabling the vector to replicate in the host cell in question. An example of such a sequence (when the host cell is a mammalian cell) is the SV 40 origin of replication, or (when the host cell is a yeast cell) the yeast plasmid 2 μ replication genes REP 1–3 and origin of replication. The vector may also comprise a selectable marker, e.g. a gene the product of which complements a defect in the host cell, such as the gene coding for dihydrofolate reductase (DHFR) or one which confers resistance to a drug, e.g. neomycin, hygromycin or methotrexate, or the *Schizosaccharomyces pombe* TPI gene (described by P. R. Russell, *Gene* 40, 1985, pp. 125–130.

The procedures used to ligate the DNA sequences coding for the inhibitor of the invention, the promoter and the terminator, respectively, and to insert them into suitable vectors containing the information necessary for replication, are well known to persons skilled in the art (cf., for instance, Sambrook et al., *Molecular Cloning: A Laboratory Manual*, Cold Spring Harbor, N.Y., 1989).

The host cell into which the expression vector of the invention is introduced may be any cell which is capable of producing the inhibitor of the invention and is preferably a eukaryotic cell, such as a mammalian, yeast or fungal cell.

The yeast organism used as the host cell according to the invention may be any yeast organism which, on cultivation, produces large quantities of the inhibitor of the invention. Examples of suitable yeast organisms are strains of the yeast species *Saccharomyces cerevisiae, Saccharomyces kluyveri, Schizosaccharomyces pombe* or *Saccharomyces uvarum.* The transformation of yeast cells may for instance be effected by protoplast formation followed by transformation in a manner known per se.

Examples of suitable mammalian cell lines are the COS (ATCC CRL 1650), BHK (ATCC CRL 1632, ATCC CCL 10) or CHO (ATCC CCL 61) cell lines. Methods of transfecting mammalian cells and expressing DNA sequences introduced in the cells are described in e.g. Kaufman and Sharp, *J. Mol. Biol.* 159, 1982, pp. 601–621; Southern and Berg, *J. Mol. Appl. Genet.* 1, 1982, pp. 327–341; Loyter et al., *Proc. Natl. Acad. Sci. U.S.A.* 79, 1982, pp. 422–426; Wigler et al., *Cell* 14, 1978, p. 725; Corsaro and Pearson, *Somatic Cell Genetics* 7, 1981, p. 603, Graham and van der Eb, *Virology* 52, 1973, p. 456; and Neumann et al., *EMBO J.* 1, 1982, pp. 841–845.

Alternatively, fungal cells may be used as host cells of the invention. Examples of suitable fungal cells are cells of filamentous fungi, e.g. Aspergillus spp. or Neurospora spp., in particular strains of *Aspergillus oryzae* or *Aspergillus niger.* The use of Aspergillus spp. for the expression of proteins is described in, e.g., EP 238 023.

The present invention further relates to a method of producing an inhibitor according to the invention, the method comprising culturing a cell as described above under conditions conducive to the expression of the inhibitor and recovering the resulting inhibitor from the culture.

The medium used to cultivate the cells may be any conventional medium suitable for growing mammalian cells or fungal (including yeast) cells, depending on the choice of host cell. The inhibitor will be secreted by the host cells to the growth medium and may be recovered therefrom by conventional procedures including separating the cells from the medium by centrifugation or filtration, precipitating the proteinaceous components of the supernatant or filtrate by means of a salt, e.g. ammonium sulfate, purification by a variety of chromatographic procedures, e.g. ion exchange chromatography or affinity chromatography, or the like.

The present invention also relates to a pharmaceutical composition comprising HKI B9 or a variant thereof of the invention together with a pharmaceutically acceptable carrier or excipient. In the composition of the invention, the variant may be formulated by any of the established methods of formulating pharmaceutical compositions, e.g. as described in *Remington's Pharmaceutical Sciences*, 1985. The composition may typically be in a form suited for systemic injection or infusion and may, as such, be formulated with sterile water or an isotonic saline or glucose solution.

HKI B9 or a variant thereof of the invention is therefore contemplated to be advantageous to use for the therapeutic applications suggested for native aprotinin or aprotinin analogues with other inhibitor profiles, in particular those which necessitate the use of large aprotinin doses. Therapeutic applications for which the use of the variant of the invention is indicated as a result of its ability to inhibit human serine proteases, e.g. trypsin, plasmin, kallikrein, elastase, cathepsin G and proteinase-3, include (but are not limited to) acute pancreatitis, inflammation, thrombocytopenia, preservation of platelet function, organ preservation, wound healing, shock (including shock lung) and conditions involving hyperfibrinolytic hemorrhage, emphysema, rheumatoid arthritis, adult respiratory distress syndrome, chronic inflammatory bowel disease and psoriasis, in other words diseases presumed to be caused by pathological proteolysis by elastase, cathepsin G and proteinase-3 released from triggered PMNs.

Apart from the pharmaceutical use indicated above, HKI B9 or a variant thereof as specified above may be used to isolate useful natural substances, e.g. proteases or receptors from human material, which bind directly or indirectly to TFPI Kunitz-type domain II, for instance by means of screening assays or by affinity chromatography.

EXAMPLES

General Methods

Standard DNA techniques were carried out as described (Sambrook, J., Fritsch, E. F., and Maniatis, T. (1989) Molecular Cloning: A Laboratory Manual, Cold Spring Harbor Laboratory Press, Cold Spring Harbor, N.Y.). Synthetic oligonucleotides were prepared on an automatic DNA synthesizer (380B, Applied Biosystems) using phosphoramidite chemistry on a controlled pore glass support (Beaucage, S. L., and Caruthers, M. H., *Tetrahedron Letters* 22, (1981) 1859–1869). DNA sequence determinations were performed by the dideoxy chain-termination technique (Sanger, F., Micklen, S., and Coulson, A. R., Proc. Natl. Acad. Sci. U.S.A. 74 (1977) 5463–5467). Polymerase chain reactions (PCR) were performed on a DNA Thermal Cycler (Perkin Elmer Cetus).

Amino acid analysis was carried out after hydrolysis in 6M HCl at 110° C. in vacuum-sealed tubes for 24 hours. Analysis was performed on a Beckman 121MB automatic amino acid analyzer modified for microbore operation. N-terminal amino acid sequence analysis was obtained by automated Edman degradation using an Applied Biosystems 470A gas-phase sequencer. Analysis by on-line reverse phase HPLC was performed for the detection and quantitation of the liberated PTH amino acids from each sequencer cycle.

Molecular weight determination was obtained on a BIO-ION 20 plasma desorption mass spectrometer (PDMS) equipped with a flight tube of approximately 15 cm and operated in positive mode. Aliquots of 5 µl were analyzed at an accelerating voltage set to 15 kV and ions were collected for 5 million fission events. The accuracy on assigned molecular ions is approximately 0.1% for well defined peaks, otherwise somewhat less.

Example 1

Cloning of Human Kunitz-type Protease Inhibitor Domain HKIB9

A. PCR Cloning

1 µg of human placenta genomic DNA (Clontech, Palo Alto, Calif., U.S.A., cat. no. 6550-2) was used as a template in each of 18 PCR reactions with 100 pmole of "right" primer A, B, C, E, F or H and 100 pmole of "left" primer X, Y or Z, see FIG. 2. The PCR reactions were performed in a 100 µl volume using a commercial kit (GeneAmp, Perkin Elmer Cetus). The reaction mixtures were heated to 95° C. for 4 min, and then subjected to the following cycle: 95° C. for 1 min, 50° C. for 1 min, and 72° C. for 1 min. After 30 cycles the temperature was kept at 72° C. for 10 min.

The reaction mixtures were subjected to gel electrophoresis on a 2% agarose gel and 0.1 kb DNA fragments isolated. After digestion with EcoRI and XbaI ligation to the 2.8 kb EcoRI and XbaI fragment of plasmid pTZ19R (Pharmacia LKB, Uppsala, Sweden, code no. 27-4986-01, Mead, D. A., Szczesna-Skorupa, E. and Kemper, B. (1986) Prot. Engin. 1, 67–74) was performed. The ligation mixtures were used to transform a competent *E. coli* strain ($r^-$, $m^+$) selecting for ampicillin resistance. Plasmids from the resulting colonies were analyzed by digestion with EcoRI and XbaI followed by gel electrophoresis on a 2% agarose gel. DNA sequencing was performed on plasmids with inserts of approximately 91 bp.

Human Kunitz-type protease inhibitor domains were identified by a characteristic DNA sequence, TG(T/C)NNNNNNTT(T/C)NNN (SEQ ID NO:27), corresponding to a region containing codons for the invariant Cys 30 and Phe 33 (aprotinin numbering, marked with an asterisk on FIG. 1) in the correct distance from the two PCR primers used.

Apart from known human Kunitz-type protease inhibitor domains and unrelated sequences a new DNA sequence corresponding to a human Kunitz-type protease inhibitor domain, HKIB9, was identified from a PCR reaction involving primers B and Y. The DNA sequence between the two PCR primers of HKIB9 thus obtained and the corresponding amino acid sequence is given below:

T Y M T R W F F N F E T G E C E L F A     (SEQ ID NO: 28)
AACCTACATGACGCGATGGTTTTTCAACTTTGAAACTGGTGAA<u>TGT</u>GAGTTA<u>TTT</u>GCT

The characteristic DNA sequence mentioned above is underlined.

B. Library Screening

A human genomic DNA cosmid library was constructed as follows:

Human genomic DNA was isolated from human whole blood. After partial Sau3A digestion the DNA was ligated into the BamHI site of the cosmid vector pWE15 (Stratagene, La Jolla, Calif., U.S.A.). Approximately 420,000 colonies were screened using the oligonucleotide probe 4280

```
5' CAAATAACTCACATTCAC-
   CAGTTTCAAAGTTGAAAAACCATCGCGTCATGTAGGT 3'
   (SEQ ID NO:29)
``` labeled in the 5' position with $^{32}$P. Filters were hybridized overnight at 65° C. in 5×SSC, 5×Denhardt's, 0.1% SDS. Filters were then washed in 1×SSC, 0.1% SDS at 65° C. for 1 hour, and finally exposed to film. A positive cosmid was identified, and a 3.5 kb PstI fragment was isolated and subcloned into plasmid pUC18, resulting in plasmid pMb-106. DNA sequencing of pMb-106 resulted in the sequence shown in SEQ ID NO.:4.

Example 2

Production of Human Kunitz-type Protease Inhibitor Domain HKIB9 From Yeast Strain KFN-1830.

1 µg of human placenta genomic DNA (Clontech, Palo Alto, Calif., U.S.A., cat. no. 6550-2) was used as a template in a PCR reaction containing 100 pmole each of the primers N-1 (CCGTTTCTAGATTAGGTGAACTTGCAGAATTTCTC SEQ ID NO: 30) and N-2 (GCTGAGAGATTGGAGAAGAGAGATCTCCTCCCAAATGT SEQ ID NO:31). N-1 is complementary to bases no. 346–367 in the genomic DNA sequence of HKIB9 in FIG. 3 and carries a 5' extension containing a translation stop codon followed by an XbaI site. The 17 3' terminal bases of N-2 are identical to bases no. 187–207 in the genomic DNA sequence of HKIB9 in SEQ ID No. 4, and the 21 5'-terminal bases are identical to bases 215 to 235 in the synthetic leader sequence (SEQ ID No. 5) from plasmid pKFN-1000 described below.

The PCR reaction was performed in a 100 µl volume using a commercial kit (GeneAmp, Perkin Elmer Cetus) and the following cycle: 94° for 20 sec, 50° for 20 sec, and 72° for 30 sec. After 19 cycles a final cycle was performed in which the 72° step was maintained for 10 min. The PCR product, a 215 bp fragment, was isolated by electrophoresis on a 2% agarose gel.

Signal-leader: 0.1 µg of a 0.7 kb PvuII fragment from pKFN-1000 described below was used as a template in a PCR reaction containing 100 pmole each of the primers NOR-1478 (GTAAAACGACGGCCAGT SEQ ID NO:32) and NOR-2523 (TCTCTTCTCCAATCTCTCAGC SEQ ID NO:33). NOR-1478 is matching a sequence just upstream of the EcoRI site in SEQ ID NO. 6. Primer NOR-2523 is complementary to the 17 3'-terminal bases of the synthetic leader gene of pKFN-1000, see SEQ ID NO. 6. The PCR reaction was performed as described above, resulting in a 257 bp fragment.

Plasmid pKFN-1000 is a derivative of plasmid pTZ19R (Mead, D. A., Szczesna-Skorupa, E. and Kemper, B., Prot. Engin. 1 (1986) 67–74) containing DNA encoding a synthetic yeast -signal-leader peptide. Plasmid pKFN-1000 is described in WO 90/10075. The DNA sequence of 235 bp downstream from the EcoRI site of pKFN-1000 and the encoded amino acid sequence of the synthetic yeast signal-leader is given in SEQ ID NO. 6.

Signal-leader-HKIB9: Approx. 0.1 µg of each of the two PCR-fragments described above were mixed. A PCR reaction was performed using 100 pmole each of primers NOR-1478 and N-1 and the following cycle: 940 for 1 min, 50° for 2 min, and 71° for 3 min. After 16 cycles a final cycle was performed in which the 72° step was maintained for 10 min.

The resulting 451 bp fragment was purified by electrophoresis on a 1% agarose gel and then digested with EcoRI and XbaI. The resulting 418 bp fragment was ligated to the 2.8 kb EcoRI-XbaI fragment from plasmid pTZ19R. The ligation mixture was used to transform a competent E. coli strain (r⁻, m⁺) selecting for ampicillin resistance. DNA sequencing showed that plasmids from the resulting colonies contained the DNA sequence for HKIB9 correctly fused to the synthetic yeast signal-leader gene. One plasmid pKFN-1826 was selected for further use.

The 418 bp EcoRI-XbaI fragment from pKFN-1826 was ligated to the 9.5 kb NcoI-XbaI fragment from pMT636 and the 1.4 kb NcoI-EcoRI fragment from pMT636, resulting in plasmid pKFN-1827.

Plasmid pMT636 is described in International Patent application No. PCT/DK88/00138. pMT636 is an E. coli—S. cerevisiae shuttle vector containing the Schizosaccharomyces pombe TPI gene (POT) (Russell, P. R., Gene 40 (1985) 125–130), the S. cerevisiae triosephosphate isomerase promoter and terminator, $TPI_P$ and $TPI_T$ (Alber, T., and Kawasaki, G. J. Mol. Appl. Gen. 1 (1982), 419–434).

The expression cassette of plasmid pKFN-1827 contains the following sequence:

$TPI_P$—KFN1000 signal-leader—HKIB9—$TPI_T$

The construction of plasmid pKFN-1827 is illustrated in FIG. 3.

The DNA sequence of the 424 bp EcoRI-XbaI fragment from pKFN-1827 is shown in SEQ ID NO. 8.

Yeast transformation: S. cerevisiae strain MT663 (E2-7B XE11-36 a/α, Δtpi/Δtpi, pep 4-3/pep 4-3) was grown on YPGaL (1% Bacto yeast extract, 2% Bacto peptone, 2% galactose, 1% lactate) to an O.D. at 600 nm of 0.6.

100 ml of culture was harvested by centrifugation, washed with 10 ml of water, recentrifugated and resuspended in 10 ml of a solution containing 1.2M sorbitol, 25 mM Na$_2$EDTA pH =8.0 and 6.7 mg/ml dithiotreitol. The suspension was incubated at 30° C. for 15 minutes, centrifuged and the cells resuspended in 10 ml of a solution containing 1.2M sorbitol, 10mM Na$_2$EDTA, 0.1M sodium citrate, pH=5.8, and 2 mg Novozym® 234. The suspension was incubated at 30° C. for 30 minutes, the cells collected by centrifugation, washed in 10 ml of 1.2M sorbitol and 10 ml of CAS (1.2M sorbitol,10 mM CaCl$_2$, 10 mM Tris HCl (Tris=Tris(hydroxymethyl)aminomethane) pH=7.5) and resuspended in 2 ml of CAS. For transformation, 0.1 ml of CAS-resuspended cells were mixed with approx. 1 µg of plasmid pKFN-1827 and left at room temperature for 15 minutes. 1 ml of (20% polyethylene glycol 4000, 20 mM CaCl$_2$, 10 mM CaCl$_2$, 10 mM Tris HCl, pH=7.5) was added and the mixture left for a further 30 minutes at room temperature. The mixture was centrifuged and the pellet resuspended in 0.1 ml of SOS (1.2M sorbitol, 33% v/v YPD, 6.7 mM CaCl$_2$, 14 µg/ml leucine) and incubated at 30° C. for 2 hours. The suspension was then centrifuged and the pellet resuspended in 0.5 ml of 1.2M sorbitol. Then, 6 ml of top agar (the SC medium of Sherman et al., (*Methods in Yeast Genetics,* Cold Spring Harbor Laboratory (1982)) containing 1.2M sorbitol plus 2.5% agar) at 52° C. was added and the suspension poured on top of plates containing the same agar-solidified, sorbitol containing medium.

Transformant colonies were picked after 3 days at 30° C., reisolated and used to start liquid cultures. One such transformant KFN-1830 was selected for further characterization. Fermentation: Yeast strain KFN-1830 was grown on YPD medium (1% yeast extract, 2% peptone (from Difco Laboratories), and 3% glucose). A 200 ml culture of the strain was shaken at 30° C. to an optical density at 650 nm of 24. After centrifugation the supernatant was isolated.

The yeast supernatant was adjusted to pH 3.0 with 5% acetic acid and phosphoric acid and applied a column of S-Sepharose Fast Flow (Pharmacia) and equilibrated with 50 mM formic acid, pH 3.7. After wash with equilibration buffer, the HKI-domain was eluted with 1M sodium chloride. Desalting was obtained on a Sephadex G-25 column (Pharmacia) equilibrated and eluted with 0.1% ammonium hydrogen carbonate, pH 7.9. After concentration by vacuum centrifugation and adjustment of pH 3.0 further purification was performed on a Mono S column (Pharmacia) equilibrated with 50 mM formic acid, pH 3.7. After washing with equilibration buffer, gradient elution was carried out from 0–1M sodium chloride in equilibration buffer. Final purification was performed by reverse phase HPLC on a Vydac C4 column (The Separation Group, CA) with gradient elution from 5–55% acetonitrile, 0.1% TFA. The purified product was lyophilized by vacuum centrifugation and redissolved in water.

Aliquots were analysed by mass PD-mass spectrometry (found: MW 6853.5, calculated: MW 6853-8) and N-terminal amino acid sequencing for 45 Edman degradation cycles confirmed the primary structure of the HKI B9 domain.

Example 3

Multiple Mutation of HKIB9 in Position 15 and 16

0.1 µg of the 1.3 kb SphI-BamHI fragment encoding HKIB9 from plasmid pKFN-1827 was used as a template in two PCR reactions. In the first PCR reaction 100 pmole each of the primers NOR-2022 (GGAGTTTAGTGAACTTGC SEQ ID NO:34)) and M-752 (GAAAAACCATCGCGT-CATGTAG(C/G)C(C/G)A(A/C)ACAAGGGC SEQ ID NO:35) was used. In the second PCR reaction 100 pmole each of the primers NOR-1495 (TAAGTGGCTCA-GAATGA SEQ ID NO:36) and M-751 (GCCCTTGT(T/G)T(C/G)G(C/G)CTACATGACGCGATGGTTTTTC SEQ ID NO:37) was used. NOR-2022 primes at a position 94 bp downstream of the SphI site. M-752 is complementary to the HKIB9 DNA-sequence position 276–310 of SEQ ID NO. 8 except for five mismatches. NOR-1495 primes at a position 561 bp upstream from the BamHI site. M-751 is complementary to M-752.

The PCR reaction was performed in a 100 µl volume using a commercial kit (GeneAmp, Perkin Elmer Cetus) and the following cycle: 95° for 1 min, 50° for 1 min, and 72° for 2 min. After 24 cycles a final cycle was performed in which the 72° step was maintained for 10 min. The PCR products, a 449 bp fragment from the first PCR and a 279 bp fragment from the second, were isolated by electrophoresis on a 2 % agarose gel.

Approx. 0.1 µg of each of the two PCR-fragments described above were mixed. A PCR reaction was performed using 100 pmole each of primers NOR-2022 and NOR-1495 and the following cycle: 95° for 1 min, 50° for 2 min, and 72° for 3 min. After 22 cycles a final cycle was performed in which the 72° step was maintained for 10 min.

The resulting 693 bp fragment was purified by electrophoresis on a 1% agarose gel and then digested with EcoRI and XbaI. The resulting 418 bp fragment was ligated to the 2.8 kb EcoRI-XbaI fragment from plasmid pTZ19R (Mead, D. A., Szczesna-Skopura, E., and Kemper, B. Prot. Engin. 1 (1986) 67–74).

The ligation mixture was used to transform a competent *E. coli* strain r⁻, m⁺) selecting for ampicillin resistance. By DNA sequencing the following five plasmids encoding the indicated HKIB9 analogs fused to the synthetic yeast signal-leader gene were identified:

| Plasmid | Analog |
| --- | --- |
| pKFN-1892 | [Q15V, T16G]-HKIB9 |
| pKFN-1916 | [Q15V, T16A]-HKIB9 |
| pKFN-1909 | [Q15F, T16G]-HKIB9 |
| pKFN-1912 | [Q15F, T16A]-HKIB9 |
| pKFN-1913 | [Q15L, T16A]-HKIB9 |

The 418 bp EcoRI-XbaI fragments from these plasmids were used for the construction of the expression plasmids as described in example 2.

Transformation of yeast strain MT-663 as described in example 2 resulted in the following yeast strains:

| Yeast Strain | Analog |
| --- | --- |
| KFN-1902 | [Q15V, T16G]-HKIB9 |
| KFN-1930 | [Q15V, T16A]-HKIB9 |
| KFN-1932 | [Q15F, T16G]-HKIB9 |
| KFN-1965 | [Q15F, T16A]-HKIB9 |
| KFN-1966 | [Q15L, T16A]-HKIB9 |

Culturing of the transformed yeast strains in YPD-medium was performed as described in example 2.

Example 4

Production of [Q15K]-HKIB9 and [Q15K, T16A]-HKIB9 from Yeast Strains KFN-1974 and KFN-1975

0.1 µg of the 1.3 kb SphI-BamHI fragment encoding HKIB9 from plasmid pKFN-1827 was used as a template in two PCR reactions. In the first PCR reaction 100 pmole each of the primers NOR-2022 (GGAGTTTAGTGAACTTGC SEQ ID NO:39)) and M-755 (GCGTCATGTAGG(C/T)TT-TACAAGGGC SEQ ID NO:39) was used. In the second PCR reaction 100 pmole each of the primers NOR-1495 (TAAGTGGCTCAGAATGA SEQ ID NO:40) and M-759 (GCCCTTGTAAA (G/A) CCTACATGACGC SEQ ID NO:41) was used.

NOR-2022 primes at a position 94 bp downstream of the SphI site. M-755 is complementary to the HKIB9 DNA-sequence position 276–299, SEQ ID NO. 8, except for two mismatches. NOR1495 primes at a position 561 bp upstream from the BamHI site. M-759 is complementary to M-755.

The PCR reaction was performed in a 100 µl volume using a commercial kit (GeneAmp, Perkin Elmer Cetus) and the following cycle: 95° for 1 min, 50° for 1 min, and 72° for 2 min. After 24 cycles a final cycle was performed in which the 72° step was maintained for 10 min. The PCR products, a 438 bp fragment from the first PCR and a 279 bp fragment from the second, were isolated by electrophoresis on a 2% agarose gel.

Approx. 0.1 µg of each of the two PCR-fragments described above were mixed. A PCR reaction was performed using 100 pmole each of primers NOR-2022 and NOR-1495 and the following cycle: 95° for 1 min, 50° for 2 min, and 72° for 3 min. After 22 cycles a final cycle was performed in which the 72° step was maintained for 10 min.

The resulting 693 bp fragment was purified by electrophoresis on a 1% agarose gel and then digested with EcoRI and XbaI. The resulting 418 bp fragment was ligated to the 2.8 kb EcoRI-XbaI fragment from plasmid pTZ19R (Mead, D. A., Szczesna-Skopura, E., and Kemper, B. Prot. Engin. 1 (1986) 67–74).

The ligation mixture was used to transform a competent E. coli strain r⁻, m⁺) selecting for ampicillin resistance. By DNA sequencing the following two plasmids encoding the indicated HKIB9 analogs fused to the synthetic yeast signal-leader gene were identified:

| Plasmid | Analog |
| --- | --- |
| pKFN-1919 | [Q15K]-HKIB9 |
| pKFN-1921 | [Q15K, T16A]-HKIB9 |

The 418 bp EcoRI-XbaI fragments from these plasmids were used for the construction of the expression plasmids as described in example 2.

Transformation of yeast strain MT-663 as described in example 2 resulted in the following yeast strains:

| Yeast Strain | Analog |
| --- | --- |
| KFN-1974 | [Q15K]-HKIB9 |
| KFN-1975 | [Q15K, T16A]-HKIB9 |

Culturing of the transformed yeast strains in YPD-medium was performed as described in example 2.

Example 5

Inhibition of Serine Proteinases by HKIB9 Variants KFN 1902 and 1930

The Kunitz domain variants were purified from yeast culture medium by the method described in example 2.

Their concentration was determined from the absorbance at 214 nm using aprotinin as a standard. Porcine trypsin was obtained from Novo Nordisk A/S, bovine chymotrypsin (TLCK treated) was obtained from Sigma Chemical Co. (St. Louis, Mo., U.S.A.). Human neutrophil cathepsin G and elastase were purified from extracts of PMNs according to the method described by Baugh and Travis, *Biochemistry* 15, 1976, pp. 836–843.

Peptidyl nitroanilide substrates S2251 and S2586 were obtained from Kabi (Stockholm, Sweden). S7388 and M4765 were obtained from Sigma Chemical Co.

Serine proteinases were incubated with various concentrations of the variants for 30 minutes. Substrate was then added and residual proteinase activity was measured at 405 nm.

KFN 1902 and KFN 1930 were found to be inhibitors of neutrophil elastase, $K_i$=140 nm and 64 nM, respectively, and to slightly inhibit chymotrypsin (5%) at 1 μM, but not to inhibit trypsin and cathepsin G under these conditions.

The experiment shows that it is possible to convert a Kunitz domain with no known inhibitory function into an elastase inhibitor.

We claim:

1. A variant of a human Kunitz-type protease inhibitor comprising a variant of SEQ ID NO:2 having the sequence Asp Leu Leu Pro Asn Val Cys Ala Phe Pro Met Glu Lys Gly Pro Cys $Xaa^4$ $Xaa^5$ Tyr Met Thr Arg Trp Phe Phe Asn Phe Glu Thr Gly Glu Cys Glu Leu Phe Ala Tyr Gly Gly Cys Gly Gly Asn Ser Asn Asn Phe Leu Arg Lys Glu Lys Cys Glu Lys Phe Cys Lys Phe Thr;

in which $Xaa^4$ is Val, Leu, Lys, Ile, Thr, Gln or Arg; and $Xaa^5$ is Thr, Gly or Ala.

2. A variant according to claim 1 which inhibits at least one of the proteases selected from the group consisting of chymotrypsin, elastase, cathepsin G, plasmin and trypsin.

3. A variant according to claim 1 in which $Xaa^4$ is Val and $Xaa^5$ is Gly; $Xaa^4$ is Val and $Xaa^5$ is Ala; $Xaa^4$ is Leu and $Xaa^5$ is Ala; $Xaa^4$ is Lys and $Xaa^5$ is Thr; or $Xaa^4$ is Lys and $Xaa^5$ is Ala.

4. A DNA construct comprising a DNA sequence encoding a human Kunitz-type protease inhibitor according to claim 1.

5. A recombinant expression vector comprising a DNA construct according to claim 4.

6. A yeast cell containing a DNA construct according to claim 4.

7. A yeast cell containing an expression vector according to claim 5.

8. A DNA construct comprising a DNA sequence encoding a human Kunitz-type protease inhibitor according to claim 3.

9. A recombinant expression vector comprising a DNA construct according to claim 8.

10. A yeast cell containing a DNA construct according to claim 8.

11. A yeast cell containing an expression vector according to claim 9.

12. A method for producing a human Kunitz-type protease inhibitor according to claim 1, the method comprising culturing a cell according to claim 6 under conditions conducive to the expression of the protein and recovering the resulting protein from the culture.

13. A method for producing a human Kunitz-type protease inhibitor according to claim 1, the method comprising culturing a cell according to claim 7 under conditions conducive to the expression of the protein and recovering the resulting protein from the culture.

14. A method for producing a human Kunitz-type protease inhibitor according to claim 3, the method comprising culturing a cell according to claim 10 under conditions conducive to the expression of the protein and recovering the resulting protein from the culture.

15. A method for producing a human Kunitz-type protease inhibitor according to claim 3, the method comprising culturing a cell according to claim 11 under conditions conducive to the expression of the protein and recovering the resulting protein from the culture.

16. A pharmaceutical composition comprising a human Kunitz-type protease inhibitor according to claim 1 and a pharmaceutically acceptable carrier or excipient.

17. A pharmaceutical composition comprising a human Kunitz-type protease inhibitor according to claim 3 and a pharmaceutically acceptable carrier or excipient.

* * * * *

SEQUENCE LISTING ( 1 ) GENERAL INFORMATION:

( i i i ) NUMBER OF SEQUENCES: 41

( 2 ) INFORMATION FOR SEQ ID NO: 1:

( i ) SEQUENCE CHARACTERISTICS:
( A ) LENGTH: 60 amino acids
( B ) TYPE: amino acid
( D ) TOPOLOGY: linear ( i i ) MOLECULE TYPE: protein ( v i ) ORIGINAL SOURCE:
( A ) ORGANISM: Homo sapiens ( x i ) SEQUENCE DESCRIPTION: SEQ ID NO: 1:

```
Asp Leu Leu Pro Asn Val Cys Ala Phe Pro Met Glu Lys Gly Pro Cys
 1               5                  10                  15
Gln Thr Tyr Met Thr Arg Trp Phe Phe Asn Phe Glu Thr Gly Glu Cys
                 20                  25                  30
Glu Leu Phe Ala Tyr Gly Gly Cys Gly Gly Asn Ser Asn Asn Phe Leu
             35                  40                  45
Arg Lys Glu Lys Cys Glu Lys Phe Cys Lys Phe Thr
         50                  55                  60
```

( 2 ) INFORMATION FOR SEQ ID NO: 2:

( i ) SEQUENCE CHARACTERISTICS:
( A ) LENGTH: 57 amino acids
( B ) TYPE: amino acid
( D ) TOPOLOGY: linear ( i i ) MOLECULE TYPE: peptide ( v i ) ORIGINAL SOURCE:
    ( A ) ORGANISM: synthetic ( x i ) SEQUENCE DESCRIPTION: SEQ ID NO: 2:

```
Xaa  Asn  Val  Cys  Ala  Phe  Pro  Met  Glu  Xaa  Gly  Xaa  Cys  Xaa  Xaa  Xaa
 1              5                        10                        15

Xaa  Xaa  Xaa  Trp  Phe  Phe  Asn  Phe  Glu  Thr  Gly  Glu  Cys  Glu  Leu  Phe
              20                        25                        30

Xaa  Tyr  Gly  Gly  Cys  Xaa  Xaa  Xaa  Ser  Asn  Asn  Phe  Xaa  Xaa  Xaa  Glu
          35                        40                        45

Lys  Cys  Glu  Lys  Phe  Cys  Lys  Phe  Xaa
 50                       55
```

( 2 ) INFORMATION FOR SEQ ID NO: 3:

( i ) SEQUENCE CHARACTERISTICS:
        ( A ) LENGTH: 60 amino acids
        ( B ) TYPE: amino acid
        ( D ) TOPOLOGY: linear ( i i ) MOLECULE TYPE: protein ( v i ) ORIGINAL SOURCE:
        ( A ) ORGANISM: synthetic ( x i ) SEQUENCE DESCRIPTION: SEQ ID NO: 3:

```
Asp  Leu  Leu  Pro  Asn  Val  Cys  Ala  Phe  Pro  Met  Glu  Lys  Gly  Pro  Cys
 1              5                        10                        15

Lys  Ala  Arg  Ile  Ile  Arg  Trp  Phe  Phe  Asn  Phe  Glu  Thr  Gly  Glu  Cys
              20                        25                        30

Glu  Leu  Phe  Val  Tyr  Gly  Gly  Cys  Arg  Ala  Lys  Ser  Asn  Asn  Phe  Lys
          35                        40                        45

Ser  Lys  Glu  Lys  Cys  Glu  Lys  Phe  Cys  Lys  Phe  Thr
 50                       55                        60
```

( 2 ) INFORMATION FOR SEQ ID NO: 4:

( i ) SEQUENCE CHARACTERISTICS:
        ( A ) LENGTH: 502 base pairs
        ( B ) TYPE: nucleic acid
        ( C ) STRANDEDNESS: single
        ( D ) TOPOLOGY: linear ( i i ) MOLECULE TYPE: DNA (genomic)

( v i ) ORIGINAL SOURCE:
        ( A ) ORGANISM: Homo sapiens ( i x ) FEATURE:
        ( A ) NAME/KEY: CDS
        ( B ) LOCATION: 187..366

( x i ) SEQUENCE DESCRIPTION: SEQ ID NO: 4:

```
AAATGTCAAC  TTCTGTGTAG  ACAGATCAGA  CCATAGCTGG  GTAGAAAGAG  GTACAGAGCA     60

CAGCCATTGT  GGATGGCCTC  ACAATTGTGC  CCAGGGCTGT  CACAGCCCCT  GGCATATGAG    120

GCAAACAAGG  AGAAGGTGAT  GGGTTTGGTC  TCCTTCAACC  ACTTTCTCTC  TTCAGACACT    180

ATCAAG  GAT  CTC  CTC  CCA  AAT  GTA  TGC  GCT  TTT  CCT  ATG  GAA  AAG  GGC    228
        Asp  Leu  Leu  Pro  Asn  Val  Cys  Ala  Phe  Pro  Met  Glu  Lys  Gly
         1              5                        10

CCT  TGT  CAA  ACC  TAC  ATG  ACG  CGA  TGG  TTT  TTC  AAC  TTT  GAA  ACT  GGT    276
Pro  Cys  Gln  Thr  Tyr  Met  Thr  Arg  Trp  Phe  Phe  Asn  Phe  Glu  Thr  Gly
 15                       20                        25                        30
```

```
GAA TGT GAG TTA TTT GCT TAC GGA GGC TGC GGA GGC AAC AGC AAC AAC      324
Glu Cys Glu Leu Phe Ala Tyr Gly Gly Cys Gly Gly Asn Ser Asn Asn
                 35                  40                  45

TTT TTG AGG AAA GAA AAA TGT GAG AAA TTC TGC AAG TTC ACC              366
Phe Leu Arg Lys Glu Lys Cys Glu Lys Phe Cys Lys Phe Thr
             50                  55                  60

TGATTTTCTA ACAAGAACAC AGCCCTCCAT GGATTCGGGA TTGCTCTGAG GGCCATAGAA    426

GGCATTTGCG TGTGTGTGTG TGTGTGTGTG TGAACAAGAG GTTCATTTCC TCTACCCCCA    486

CATTTATTCT CCCTGA                                                    502
```

( 2 ) INFORMATION FOR SEQ ID NO: 5:

( i ) SEQUENCE CHARACTERISTICS:
        ( A ) LENGTH: 60 amino acids
        ( B ) TYPE: amino acid
        ( D ) TOPOLOGY: linear ( i i ) MOLECULE TYPE: protein ( x i ) SEQUENCE DESCRIPTION: SEQ ID NO: 5:

```
Asp Leu Leu Pro Asn Val Cys Ala Phe Pro Met Glu Lys Gly Pro Cys
 1               5                  10                  15

Gln Thr Tyr Met Thr Arg Trp Phe Phe Asn Phe Glu Thr Gly Glu Cys
             20                  25                  30

Glu Leu Phe Ala Tyr Gly Gly Cys Gly Gly Asn Ser Asn Asn Phe Leu
             35                  40                  45

Arg Lys Glu Lys Cys Glu Lys Phe Cys Lys Phe Thr
         50                  55                  60
```

( 2 ) INFORMATION FOR SEQ ID NO: 6:

( i ) SEQUENCE CHARACTERISTICS:
        ( A ) LENGTH: 235 base pairs
        ( B ) TYPE: nucleic acid
        ( C ) STRANDEDNESS: single
        ( D ) TOPOLOGY: linear ( i i ) MOLECULE TYPE: cDNA ( v i ) ORIGINAL SOURCE:
        ( A ) ORGANISM: synthetic ( i x ) FEATURE:
        ( A ) NAME/KEY: CDS
        ( B ) LOCATION: 77..235

( x i ) SEQUENCE DESCRIPTION: SEQ ID NO: 6:

```
GAATTCCATT CAAGAATAGT TCAAACAAGA AGATTACAAA CTATCAATTT CATACACAAT    60

ATAAACGACC AAAAGA ATG AAG GCT GTT TTC TTG GTT TTG TCC TTG ATC       109
               Met Lys Ala Val Phe Leu Val Leu Ser Leu Ile
                1               5                  10

GGA TTC TGC TGG GCC CAA CCA GTC ACT GGC GAT GAA TCA TCT GTT GAG    157
Gly Phe Cys Trp Ala Gln Pro Val Thr Gly Asp Glu Ser Ser Val Glu
             15                  20                  25

ATT CCG GAA GAG TCT CTG ATC ATC GCT GAA AAC ACC ACT TTG GCT AAC    205
Ile Pro Glu Glu Ser Leu Ile Ile Ala Glu Asn Thr Thr Leu Ala Asn
         30                  35                  40

GTC GCC ATG GCT GAG AGA TTG GAG AAG AGA                            235
Val Ala Met Ala Glu Arg Leu Glu Lys Arg
         45                  50
```

( 2 ) INFORMATION FOR SEQ ID NO: 7:

( i ) SEQUENCE CHARACTERISTICS:
  ( A ) LENGTH: 53 amino acids
  ( B ) TYPE: amino acid
  ( D ) TOPOLOGY: linear ( i i ) MOLECULE TYPE: protein ( x i ) SEQUENCE DESCRIPTION: SEQ ID NO: 7:

```
Met Lys Ala Val Phe Leu Val Leu Ser Leu Ile Gly Phe Cys Trp Ala
 1               5                  10                  15

Gln Pro Val Thr Gly Asp Glu Ser Ser Val Glu Ile Pro Glu Glu Ser
            20                  25                  30

Leu Ile Ile Ala Glu Asn Thr Thr Leu Ala Asn Val Ala Met Ala Glu
            35                  40                  45

Arg Leu Glu Lys Arg
        50
```

( 2 ) INFORMATION FOR SEQ ID NO: 8:

( i ) SEQUENCE CHARACTERISTICS:
    ( A ) LENGTH: 424 base pairs
    ( B ) TYPE: nucleic acid
    ( C ) STRANDEDNESS: single
    ( D ) TOPOLOGY: linear ( i i ) MOLECULE TYPE: cDNA ( v i ) ORIGINAL SOURCE:
    ( A ) ORGANISM: synthetic/human ( i x ) FEATURE:
    ( A ) NAME/KEY: sig_peptide
    ( B ) LOCATION: 77..235

( i x ) FEATURE:
    ( A ) NAME/KEY: mat_peptide
    ( B ) LOCATION: 236..415

( i x ) FEATURE:
    ( A ) NAME/KEY: CDS
    ( B ) LOCATION: 77..415

( x i ) SEQUENCE DESCRIPTION: SEQ ID NO: 8:

```
GAATTCCATT CAAGAATAGT TCAAACAAGA AGATTACAAA CTATCAATTT CATACACAAT        60

ATAAACGACC AAAAGA ATG AAG GCT GTT TTC TTG GTT TTG TCC TTG ATC          109
               Met Lys Ala Val Phe Leu Val Leu Ser Leu Ile
               -53           -50                      -45

GGA TTC TGC TGG GCC CAA CCA GTC ACT GGC GAT GAA TCA TCT GTT GAG        157
Gly Phe Cys Trp Ala Gln Pro Val Thr Gly Asp Glu Ser Ser Val Glu
        -40                 -35                     -30

ATT CCG GAA GAG TCT CTG ATC ATC GCT GAA AAC ACC ACT TTG GCT AAC        205
Ile Pro Glu Glu Ser Leu Ile Ile Ala Glu Asn Thr Thr Leu Ala Asn
    -25                 -20                     -15

GTC GCC ATG GCT GAG AGA TTG GAG AAG AGA GAT CTC CTC CCA AAT GTA        253
Val Ala Met Ala Glu Arg Leu Glu Lys Arg Asp Leu Leu Pro Asn Val
-10                  -5                   1                   5

TGC GCT TTT CCT ATG GAA AAG GGC CCT TGT CAA ACC TAC ATG ACG CGA        301
Cys Ala Phe Pro Met Glu Lys Gly Pro Cys Gln Thr Tyr Met Thr Arg
                 10                  15                  20

TGG TTT TTC AAC TTT GAA ACT GGT GAA TGT GAG TTA TTT GCT TAC GGA        349
Trp Phe Phe Asn Phe Glu Thr Gly Glu Cys Glu Leu Phe Ala Tyr Gly
             25                  30                  35

GGC TGC GGA GGC AAC AGC AAC AAC TTT TTG AGG AAA GAA AAA TGT GAG        397
Gly Cys Gly Gly Asn Ser Asn Asn Phe Leu Arg Lys Glu Lys Cys Glu
         40                  45                  50

AAA TTC TGC AAG TTC ACC TAATCTAGA                                      424
Lys Phe Cys Lys Phe Thr
```

Lys Phe Cys Lys Phe Thr
55                    60

( 2 ) INFORMATION FOR SEQ ID NO: 9:

( i ) SEQUENCE CHARACTERISTICS:
        ( A ) LENGTH: 113 amino acids
        ( B ) TYPE: amino acid
        ( D ) TOPOLOGY: linear ( i i ) MOLECULE TYPE: protein ( x i ) SEQUENCE DESCRIPTION: SEQ ID NO: 9:

Met Lys Ala Val Phe Leu Val Leu Ser Leu Ile Gly Phe Cys Trp Ala
-53         -50              -45                 -40

Gln Pro Val Thr Gly Asp Glu Ser Ser Val Glu Ile Pro Glu Glu Ser
        -35              -30                 -25

Leu Ile Ile Ala Glu Asn Thr Thr Leu Ala Asn Val Ala Met Ala Glu
    -20              -15                 -10

Arg Leu Glu Lys Arg Asp Leu Leu Pro Asn Val Cys Ala Phe Pro Met
-5               1               5                        10

Glu Lys Gly Pro Cys Gln Thr Tyr Met Thr Arg Trp Phe Phe Asn Phe
            15              20                    25

Glu Thr Gly Glu Cys Glu Leu Phe Ala Tyr Gly Gly Cys Gly Gly Asn
            30              35              40

Ser Asn Asn Phe Leu Arg Lys Glu Lys Cys Glu Lys Phe Cys Lys Phe
        45              50              55

Thr
60

( 2 ) INFORMATION FOR SEQ ID NO: 10:

( i ) SEQUENCE CHARACTERISTICS:
        ( A ) LENGTH: 58 amino acids
        ( B ) TYPE: amino acid
        ( D ) TOPOLOGY: linear ( i i ) MOLECULE TYPE: protein ( v i ) ORIGINAL SOURCE:
        ( A ) ORGANISM: Homo sapiens ( x i ) SEQUENCE DESCRIPTION: SEQ ID NO: 10:

Lys Glu Asp Ser Cys Gln Leu Gly Tyr Ser Ala Gly Pro Cys Met Gly
1               5               10                      15

Met Thr Ser Arg Tyr Phe Tyr Asn Gly Thr Ser Met Ala Cys Glu Thr
            20              25                      30

Phe Gln Tyr Gly Gly Cys Met Gly Asn Gly Asn Asn Phe Val Thr Glu
        35              40                      45

Lys Glu Cys Leu Gln Thr Cys Arg Thr Val
        50              55

( 2 ) INFORMATION FOR SEQ ID NO: 11:

( i ) SEQUENCE CHARACTERISTICS:
        ( A ) LENGTH: 58 amino acids
        ( B ) TYPE: amino acid
        ( D ) TOPOLOGY: linear ( i i ) MOLECULE TYPE: protein ( v i ) ORIGINAL SOURCE:
        ( A ) ORGANISM: Homo sapiens ( x i ) SEQUENCE DESCRIPTION: SEQ ID NO: 11:

```
        Thr  Val  Ala  Ala  Cys  Asn  Leu  Pro  Ile  Val  Arg  Gly  Pro  Cys  Arg  Ala
        1              5                        10                       15

Phe  Ile  Gln  Leu  Trp  Ala  Phe  Asp  Ala  Val  Lys  Gly  Lys  Cys  Val  Leu
                      20                       25                       30

Phe  Pro  Tyr  Gly  Gly  Cys  Gln  Gly  Asn  Gly  Asn  Lys  Phe  Thr  Ser  Glu
                      35                       40                       45

Lys  Glu  Cys  Arg  Glu  Tyr  Cys  Gly  Val  Pro
                      50                       55
```

( 2 ) INFORMATION FOR SEQ ID NO: 12:

( i ) SEQUENCE CHARACTERISTICS:
        ( A ) LENGTH: 58 amino acids
        ( B ) TYPE: amino acid
        ( D ) TOPOLOGY: linear ( i i ) MOLECULE TYPE: protein ( v i ) ORIGINAL SOURCE:
        ( A ) ORGANISM: Homo sapiens ( x i ) SEQUENCE DESCRIPTION: SEQ ID NO: 12:

```
        Val  Arg  Glu  Val  Cys  Ser  Glu  Gln  Ala  Glu  Thr  Gly  Pro  Cys  Arg  Ala
        1              5                        10                       15

Met  Ile  Ser  Arg  Trp  Tyr  Phe  Asp  Val  Thr  Glu  Gly  Lys  Cys  Ala  Pro
                      20                       25                       30

Phe  Phe  Tyr  Gly  Gly  Cys  Gly  Gly  Asn  Arg  Asn  Asn  Phe  Asp  Thr  Glu
                      35                       40                       45

Glu  Tyr  Cys  Met  Ala  Val  Cys  Gly  Ser  Ala
                      50                       55
```

( 2 ) INFORMATION FOR SEQ ID NO: 13:

( i ) SEQUENCE CHARACTERISTICS:
        ( A ) LENGTH: 58 amino acids
        ( B ) TYPE: amino acid
        ( D ) TOPOLOGY: linear ( i i ) MOLECULE TYPE: protein ( v i ) ORIGINAL SOURCE:
        ( A ) ORGANISM: Homo sapiens ( x i ) SEQUENCE DESCRIPTION: SEQ ID NO: 13:

```
        Met  His  Ser  Phe  Cys  Ala  Phe  Lys  Ala  Asp  Asp  Gly  Pro  Cys  Lys  Ala
        1              5                        10                       15

Ile  Met  Lys  Arg  Phe  Phe  Phe  Asn  Ile  Phe  Thr  Arg  Gln  Cys  Glu  Glu
                      20                       25                       30

Phe  Ile  Tyr  Gly  Gly  Cys  Glu  Gly  Asn  Gln  Asn  Arg  Phe  Glu  Ser  Leu
                      35                       40                       45

Glu  Glu  Cys  Lys  Lys  Met  Cys  Thr  Arg  Asp
                      50                       55
```

( 2 ) INFORMATION FOR SEQ ID NO: 14:

( i ) SEQUENCE CHARACTERISTICS:
        ( A ) LENGTH: 58 amino acids
        ( B ) TYPE: amino acid
        ( D ) TOPOLOGY: linear ( i i ) MOLECULE TYPE: protein ( v i ) ORIGINAL SOURCE:
        ( A ) ORGANISM: Homo sapiens ( x i ) SEQUENCE DESCRIPTION: SEQ ID NO: 14:

Lys Pro Asp Phe Cys Phe Leu Glu Glu Asp Pro Gly Ile Cys Arg Gly
1               5                   10                  15

Tyr Ile Thr Arg Tyr Phe Tyr Asn Asn Gln Thr Lys Gln Cys Glu Arg
            20              25                  30

Phe Lys Tyr Gly Gly Cys Leu Gly Asn Met Asn Asn Phe Glu Thr Leu
        35              40                  45

Glu Glu Cys Lys Asn Ile Cys Glu Asp Gly
    50              55

( 2 ) INFORMATION FOR SEQ ID NO: 15:

( i ) SEQUENCE CHARACTERISTICS:
      ( A ) LENGTH: 58 amino acids
      ( B ) TYPE: amino acid
      ( D ) TOPOLOGY: linear ( i i ) MOLECULE TYPE: protein ( v i ) ORIGINAL SOURCE:
      ( A ) ORGANISM: Homo sapiens ( x i ) SEQUENCE DESCRIPTION: SEQ ID NO: 15:

Gly Pro Ser Trp Cys Leu Thr Pro Ala Asp Arg Gly Leu Cys Arg Ala
1               5                   10                  15

Asn Glu Asn Arg Phe Tyr Tyr Asn Ser Val Ile Gly Lys Cys Arg Pro
            20              25                  30

Phe Lys Tyr Ser Gly Cys Gly Gly Asn Glu Asn Asn Phe Thr Ser Lys
        35              40                  45

Gln Glu Cys Leu Arg Ala Cys Lys Lys Gly
    50              55

( 2 ) INFORMATION FOR SEQ ID NO: 16:

( i ) SEQUENCE CHARACTERISTICS:
      ( A ) LENGTH: 58 amino acids
      ( B ) TYPE: amino acid
      ( D ) TOPOLOGY: linear ( i i ) MOLECULE TYPE: protein ( v i ) ORIGINAL SOURCE:
      ( A ) ORGANISM: Homo sapiens ( x i ) SEQUENCE DESCRIPTION: SEQ ID NO: 16:

Glu Thr Asp Ile Cys Lys Leu Pro Lys Asp Glu Gly Thr Cys Arg Asp
1               5                   10                  15

Phe Ile Leu Lys Trp Tyr Tyr Asp Pro Asn Thr Lys Ser Cys Ala Arg
            20              25                  30

Phe Trp Tyr Gly Gly Cys Gly Gly Asn Glu Asn Lys Phe Gly Ser Gln
        35              40                  45

Lys Glu Cys Glu Lys Val Cys Ala Pro Val
    50              55

( 2 ) INFORMATION FOR SEQ ID NO: 17:

( i ) SEQUENCE CHARACTERISTICS:
      ( A ) LENGTH: 58 amino acids
      ( B ) TYPE: amino acid
      ( D ) TOPOLOGY: linear ( i i ) MOLECULE TYPE: protein ( v i ) ORIGINAL SOURCE:
      ( A ) ORGANISM: Bos ( x i ) SEQUENCE DESCRIPTION: SEQ ID NO: 17:

Arg Pro Asp Phe Cys Leu Glu Pro Pro Tyr Thr Gly Pro Cys Lys Ala
1               5                       10                      15

Arg Ile Ile Arg Tyr Phe Tyr Asn Ala Lys Ala Gly Leu Cys Gln Thr
                20                  25                  30

Phe Val Tyr Gly Gly Cys Arg Ala Lys Arg Asn Asn Phe Lys Ser Ala
            35                  40                  45

Glu Asp Cys Met Arg Thr Cys Gly Gly Ala
50                      55

( 2 ) INFORMATION FOR SEQ ID NO: 18:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: Other nucleic acid ( x i ) SEQUENCE DESCRIPTION: SEQ ID NO: 18:

GTTGGAATTC GGNCCNTG Y A ARG          23

( 2 ) INFORMATION FOR SEQ ID NO: 19:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: Other nucleic acid ( x i ) SEQUENCE DESCRIPTION: SEQ ID NO: 19:

GTTGGAATTC GGNCCNTG Y C G            21

( 2 ) INFORMATION FOR SEQ ID NO: 20:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: Other nucleic acid ( x i ) SEQUENCE DESCRIPTION: SEQ ID NO: 20:

GTTGGAATTC GGNNT Y TG Y A ARG        23

( 2 ) INFORMATION FOR SEQ ID NO: 21:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: Other nucleic acid ( x i ) SEQUENCE DESCRIPTION: SEQ ID NO: 21:

GTTGGAATTC GGNNTRTG Y A ARG          23

( 2 ) INFORMATION FOR SEQ ID NO: 22:

( i ) SEQUENCE CHARACTERISTICS:
        ( A ) LENGTH: 21 base pairs (B) TYPE: nucleic acid
(C) STRANDEDNESS: single
(D) TOPOLOGY: linear (ii) MOLECULE TYPE: Other nucleic acid (xi) SEQUENCE DESCRIPTION: SEQ ID NO: 22:

GTTGGAATTC GGNNTYTGYC G    21

(2) INFORMATION FOR SEQ ID NO: 23:

(i) SEQUENCE CHARACTERISTICS:
(A) LENGTH: 21 base pairs
(B) TYPE: nucleic acid
(C) STRANDEDNESS: single
(D) TOPOLOGY: linear (ii) MOLECULE TYPE: Other nucleic acid (xi) SEQUENCE DESCRIPTION: SEQ ID NO: 23:

GTTGGAATTC GGNNTRTGYC G    21

(2) INFORMATION FOR SEQ ID NO: 24:

(i) SEQUENCE CHARACTERISTICS:
(A) LENGTH: 22 base pairs
(B) TYPE: nucleic acid
(C) STRANDEDNESS: single
(D) TOPOLOGY: linear (ii) MOLECULE TYPE: Other nucleic acid (xi) SEQUENCE DESCRIPTION: SEQ ID NO: 24:

GGTTTCTAGA RCANCCRCCR TA    22

(2) INFORMATION FOR SEQ ID NO: 25:

(i) SEQUENCE CHARACTERISTICS:
(A) LENGTH: 22 base pairs
(B) TYPE: nucleic acid
(C) STRANDEDNESS: single
(D) TOPOLOGY: linear (ii) MOLECULE TYPE: Other nucleic acid (xi) SEQUENCE DESCRIPTION: SEQ ID NO: 25:

GGTTTCTAGA RCANCCYCCR TA    22

(2) INFORMATION FOR SEQ ID NO: 26:

(i) SEQUENCE CHARACTERISTICS:
(A) LENGTH: 22 base pairs
(B) TYPE: nucleic acid
(C) STRANDEDNESS: single
(D) TOPOLOGY: linear (ii) MOLECULE TYPE: Other nucleic acid (xi) SEQUENCE DESCRIPTION: SEQ ID NO: 26:

GGTTTCTAGA RCANCCRCTR TA    22

(2) INFORMATION FOR SEQ ID NO: 27:

(i) SEQUENCE CHARACTERISTICS:
(A) LENGTH: 15 base pairs
(B) TYPE: nucleic acid
(C) STRANDEDNESS: single
(D) TOPOLOGY: linear (ii) MOLECULE TYPE: Other nucleic acid ( x i ) SEQUENCE DESCRIPTION: SEQ ID NO: 27:

TGYNNNNNNT TYNNN                                                                                   15

( 2 ) INFORMATION FOR SEQ ID NO: 28:

( i ) SEQUENCE CHARACTERISTICS:
        ( A ) LENGTH: 58 base pairs
        ( B ) TYPE: nucleic acid
        ( C ) STRANDEDNESS: single
        ( D ) TOPOLOGY: linear ( i i ) MOLECULE TYPE: DNA (genomic)

( v i ) ORIGINAL SOURCE:
        ( A ) ORGANISM: Homo sapiens ( x i ) SEQUENCE DESCRIPTION: SEQ ID NO: 28:

```
A ACC TAC ATG ACG CGA TGG TTT TTC AAC TTT GAA ACT GGT GAA TGT    46
  Thr Tyr Met Thr Arg Trp Phe Phe Asn Phe Glu Thr Gly Glu Cys
  1           5                   10                  15

GAG TTA TTT GCT                                                  58
Glu Leu Phe Ala
```

( 2 ) INFORMATION FOR SEQ ID NO: 29:

( i ) SEQUENCE CHARACTERISTICS:
        ( A ) LENGTH: 55 base pairs
        ( B ) TYPE: nucleic acid
        ( C ) STRANDEDNESS: single
        ( D ) TOPOLOGY: linear ( i i ) MOLECULE TYPE: Other nucleic acid ( x i ) SEQUENCE DESCRIPTION: SEQ ID NO: 29:

CAAATAACTC ACATTCACCA GTTTCAAAGT TGAAAAACCA TCGCGTCATG TAGGT                  55

( 2 ) INFORMATION FOR SEQ ID NO: 30:

( i ) SEQUENCE CHARACTERISTICS:
        ( A ) LENGTH: 35 base pairs
        ( B ) TYPE: nucleic acid
        ( C ) STRANDEDNESS: single
        ( D ) TOPOLOGY: linear ( i i ) MOLECULE TYPE: Other nucleic acid ( x i ) SEQUENCE DESCRIPTION: SEQ ID NO: 30:

CCGTTTCTAG ATTAGGTGAA CTTGCAGAAT TTCTC                                        35

( 2 ) INFORMATION FOR SEQ ID NO: 31:

( i ) SEQUENCE CHARACTERISTICS:
        ( A ) LENGTH: 38 base pairs
        ( B ) TYPE: nucleic acid
        ( C ) STRANDEDNESS: single
        ( D ) TOPOLOGY: linear ( i i ) MOLECULE TYPE: Other nucleic acid ( x i ) SEQUENCE DESCRIPTION: SEQ ID NO: 31:

GCTGAGAGAT TGGAGAAGAG AGATCTCCTC CCAAATGT                                     38

( 2 ) INFORMATION FOR SEQ ID NO: 32:

( i ) SEQUENCE CHARACTERISTICS:
        ( A ) LENGTH: 17 base pairs
        ( B ) TYPE: nucleic acid
        ( C ) STRANDEDNESS: single (D) TOPOLOGY: linear (ii) MOLECULE TYPE: Other nucleic acid (xi) SEQUENCE DESCRIPTION: SEQ ID NO: 32:

GTAAAACGAC GGCCAGT                                                                              17

(2) INFORMATION FOR SEQ ID NO: 33:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: Other nucleic acid (xi) SEQUENCE DESCRIPTION: SEQ ID NO: 33:

TCTCTTCTCC AATCTCTCAG C                                                                         21

(2) INFORMATION FOR SEQ ID NO: 34:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: Other nucleic acid (xi) SEQUENCE DESCRIPTION: SEQ ID NO: 34:

GGAGTTTAGT GAACTTGC                                                                             18

(2) INFORMATION FOR SEQ ID NO: 35:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (ii) MOLECULE TYPE: Other nucleic acid (xi) SEQUENCE DESCRIPTION: SEQ ID NO: 35:

GAAAAACCAT CGCGTCATGT AGSCSAMACA AGGGC                                                           35

(2) INFORMATION FOR SEQ ID NO: 36:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: Other nucleic acid (xi) SEQUENCE DESCRIPTION: SEQ ID NO: 36:

TAAGTGGCTC AGAATGA                                                                              17

(2) INFORMATION FOR SEQ ID NO: 37:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (ii) MOLECULE TYPE: Other nucleic acid (xi) SEQUENCE DESCRIPTION: SEQ ID NO: 37:

```
GCCCTTGTKT SGSCTACATG ACGCGATGGT TTTTC                                    35
```

( 2 ) INFORMATION FOR SEQ ID NO: 38:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: Other nucleic acid ( x i ) SEQUENCE DESCRIPTION: SEQ ID NO: 38:

```
GGAGTTTAGT GAACTTGC                                                       18
```

( 2 ) INFORMATION FOR SEQ ID NO: 39:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: Other nucleic acid ( x i ) SEQUENCE DESCRIPTION: SEQ ID NO: 39:

```
GCGTCATGTA GG Y TTTACAA GGGC                                              24
```

( 2 ) INFORMATION FOR SEQ ID NO: 40:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: Other nucleic acid ( x i ) SEQUENCE DESCRIPTION: SEQ ID NO: 40:

```
TAAGTGGCTC AGAATGA                                                        17
```

( 2 ) INFORMATION FOR SEQ ID NO: 41:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: Other nucleic acid ( x i ) SEQUENCE DESCRIPTION: SEQ ID NO: 41:

```
GCCCTTGTAA ARCCTACATG ACGC                                                24
```